(12) United States Patent
Zhang et al.

(10) Patent No.: US 11,028,360 B2
(45) Date of Patent: Jun. 8, 2021

(54) SEPARATOR FOR MICROORGANISMS IN CAVITARY CONTENTS

(71) Applicant: NANJING FMT MEDICAL CO., LTD., Jiangsu (CN)

(72) Inventors: Faming Zhang, Jiangsu (CN); Youquan Zhao, Jiangsu (CN); Huiquan Wang, Jiangsu (CN); Bota Cui, Jiangsu (CN); Pan Li, Jiangsu (CN); Guozhong Ji, Jiangsu (CN)

(73) Assignee: NANJING FMT MEDICAL CO., LTD., Jiangsu (CN)

( * ) Notice: Subject to any disclaimer, the term of this patent is extended or adjusted under 35 U.S.C. 154(b) by 644 days.

(21) Appl. No.: 15/523,645

(22) PCT Filed: Feb. 15, 2015

(86) PCT No.: PCT/CN2015/073084
§ 371 (c)(1),
(2) Date: May 1, 2017

(87) PCT Pub. No.: WO2016/065777
PCT Pub. Date: May 6, 2016

(65) Prior Publication Data
US 2017/0313971 A1   Nov. 2, 2017

(30) Foreign Application Priority Data

Oct. 31, 2014   (CN) .......................... 201410606325.4

(51) Int. Cl.
*C12M 1/00* (2006.01)
*C12M 1/26* (2006.01)

(52) U.S. Cl.
CPC ............ *C12M 47/04* (2013.01); *C12M 33/08* (2013.01); *C12M 33/14* (2013.01)

(58) Field of Classification Search
CPC ....... C12M 47/04; C12M 33/08; C12M 33/14
See application file for complete search history.

(56) References Cited

U.S. PATENT DOCUMENTS

2015/0374761 A1* 12/2015 Sadowsky ............ A61K 35/741
424/489

FOREIGN PATENT DOCUMENTS

| CN | 1931800 A | 3/2007 |
|---|---|---|
| CN | 103124559 A | 5/2013 |
| CN | 103194385 A | 7/2013 |
| CN | 103330961 A | 10/2013 |
| CN | 204311058 U | 5/2015 |

OTHER PUBLICATIONS

English translation of CN1931800 by Patent Translate Powered by EPO and Google , Accessed 2019 (Year: 2019).*

* cited by examiner

*Primary Examiner* — William H. Beisner
*Assistant Examiner* — Danielle B Henkel
(74) *Attorney, Agent, or Firm* — Muncy, Geissler, Olds & Lowe, P.C.

(57) ABSTRACT

The present invention provides a separator for microorganisms in cavitary contents. The separator for microorganisms in cavitary contents includes a raw material vessel, a stage filter, a liquid storage vessel, a closed separated material vessel, a separate loading unit, a deodorizer, pipelines for connecting all the units, etc.

Figure 1:
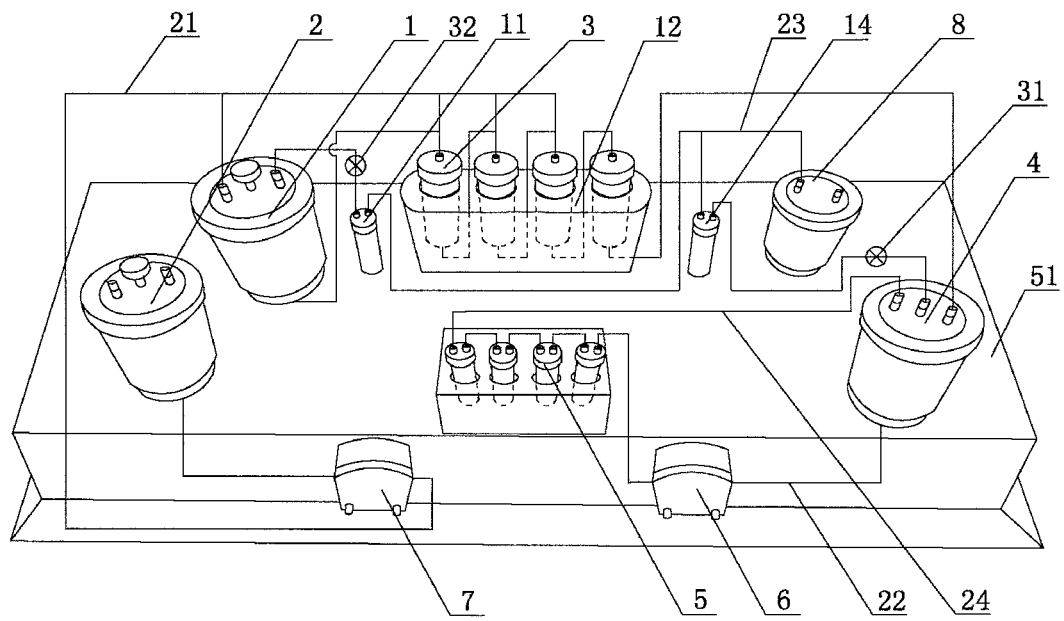

17 Claims, 2 Drawing Sheets form fecal microbiota transplantation, all these methods have the following problems: (1) medical workers who prepare fecal liquid will visually and psychologically feel uncomfortable with fecal water, and even someone may reject this work; (2) the non-standardization of preparation procedures will lead to an increase in manpower cost in treatment procedures; (3) past researches all relate to the possibility on how to prevent intestinal parasites from infecting feces, this lacks a new breakthrough in the methodology of fecal microbiota transplantation, that is, as bacterium liquid is obtained, parasite ova must be effectively filtered out to prevent parasitic infection, and at the same time, other impurities and odor also have to be filtered out

SEPARATOR FOR MICROORGANISMS IN CAVITARY CONTENTS

TECHNICAL FIELD

The present invention belongs to the technical field of medical apparatuses, and particularly relates to a separator for microorganisms in cavitary contents.

RELATED ART

Gastrointestinal contents of the human body include a variety of tangible components, such as food residue, florae and parasite ova, body fluid components secreted by the intestines, foreign matters and liquid getting into cavities for various reasons, and fine tumor tissues which are resected endoscopically but cannot be easily taken out directly. In clinical and research processes, distinguishing and obtaining these target components has to rely on an effective apparatus to assist separation. Taking the clinical background of preparing fecal microbiota transplantation bacterium liquid and collecting a large quantity of fecal ova as an example, the importance of collecting target components of cavitary contents of the human body is described briefly below.

Normal florae in the human intestines have been regarded as a special organ in the human body, and fecal microbiota transplantation is regarded as a type of special organ transplantation. There are about 1000 to 1050 species of intestinal bacteria, and as yet the functions of the vast majority of the bacteria and what kind of mechanism the different bacteria organically work in are unclear to the human being. Recently, modern medicine has become more aware of the important role of the intestinal bacteria in the human body, and has already adopted the maintenance or reconstruction of the normal florae of the human intestines as an important therapeutic approach to a variety of diseases. As for commonly used probiotic medicines and foods, only one or several species of intestinal bacteria are specially cultured in vitro, and are then packaged according to a certain quantity. However, since the number and varieties of the bacteria taken into the human intestines are very limited, their therapeutic value is also very limited. In recent five years, fecal microbiota transplantation has gradually gained attention, and especially for infection-associated diseases which medicines, such as commonly used antibiotics, fail to treat, such as antibiotic-associated diarrhea, intractable inflammatory bowel disease, intractable irritable bowel syndrome, immune-associated intractable diarrhea, obesity, food allergy, intestinal symptoms of depression and fatty liver, its therapeutic value appears to be particularly important.

As science develops up to now, although a few researches have delivered fecal suspensions or fecal bacterium suspensions into the gastrointestinal tracts via an enteroscope, a gastroscope, a nasogastric tube, a jejunum tube, a capsule and so on to implement fecal microbiota transplantation, all as much as possible; (4) conventional manual filtration measures can hardly guarantee the reliability and controllability of the quality of fecal bacterium specimens. There have been foreign clinical reports on using coffee machines to manually prepare fecal bacterium liquid. However, such a method not only wastes homogenizing and filtering equipment and consumes a lot of time and labor in the process of operation, but also is a challenging trial on the psychology of medical workers treating a bucket of feces. So far there haven't been domestic and foreign papers and patent literatures to disclose standardized apparatuses for fecal bacterium liquid preparation.

Another important clinical requirement is to collect a large number of parasite ova from feces. Finding intestinal parasite ova is a golden standard in the diagnosis of intestinal parasitic diseases. Parasitic diseases have already been rare in the developed Western countries, and the clinical requirement on parasite ovum collection hasn't been highlighted. However, in underdeveloped regions, such as China, Southeast Asia and Africa, parasitic diseases are still very common. In a typical parasite ovum examination and search method, very little feces is used to prepare a smear, and parasite ova are then searched under a microscope. Such an examination method is low in positive rate, and can easily cause the missed diagnosis of parasitic infection.

Another clinical requirement is to suck gastrointestinal fluid under an endoscope for assay, its main purpose is to obtain fluid components, but various solid components, such as food residue, will be inevitably mixed in the process of suction; moreover, the clinical requirement is to suck bladder fluid under a urethra endoscope for assay, its main purpose is to obtain the fluid and tangible components in it, such as exfoliated cells, but solid components, such as large residues including calculi in urine, may be mixed in the process of suction; furthermore, the clinical requirement is to obtain secreted fluid in the trachea and lavaging fluid, its main purpose is to obtain the fluids and tangible components in it, such as exfoliated cells, but visible tissue blocks, thick sputum and so on will be mixed in them. An apparatus for filtering out residues plays an important role for the quality and quantity of collected fluid. The clinical requirement can be met in the above-mentioned apparatus for collecting fecal bacterium liquid.

Based on the above-mentioned clinical requirements and the like, an apparatus for collecting target components of cavitary contents of the human body in vitro can be designed to widely meet a variety of clinical requirements.

SUMMARY

The objective of the present invention is to provide a device for separating microorganisms in contents, which can safely and effectively analyze microorganisms in cavitary contents, soil, rivers, lakes or silt, facilitating implementation and environmental protection for operators. It mainly can realize: (1) obtaining florae in feces and effectively removing undigested food residue, parasite ova, yellow mucus in fecal liquid and odor at the same time for fecal microbiota transplantation therapy; (2) separating and collecting a large number of parasite ova in fecal suspension for examination; (3) collecting fluid secreted in cavities and cell components via a gastrointestinal endoscope and removing gastrointestinal food residue at the same time for examination and diagnosis; (4) collecting secreted fluid in the trachea via a bronchoscope and removing thick sputum and the like at the same time for examination and diagnosis; (5) separating out microorganisms in specific soil, river, lake or silt for testing or research.

The objective of the present invention can be achieved by the following measures:

Disclosed is a separator for microorganisms in cavitary contents, and the separator includes:

a raw material vessel provided with a filling opening and an odor outlet, an agitator is arranged in the raw material vessel, the lower part or bottom of the raw material vessel is provided with a discharge outlet, and the discharge outlet is connected to an inlet of a stage filter;

a stage filter provided with a material inlet and a material outlet, the material inlet of the stage filter communicates with the discharge outlet of the raw material vessel, the stage filter mainly includes one or more stage filtration bottles, both ends of each stage filtration bottle are provided respectively with a feed inlet and a discharge outlet, and at least one layer of filter screen is arranged in each stage filtration bottle; if the stage filter includes a plurality of stage filtration bottles, all the stage filtration bottles are connected in series, parallel or series and parallel; the stage filter is arranged partially or completely in a vibrator which can rock, shake or wave liquid in the stage filtration bottles;

a liquid storage vessel provided with a liquid outlet, the liquid outlet communicates with the filling opening of the raw material vessel through a filling pipeline, or the liquid outlet communicates with both the filling opening of the raw material vessel and the feed inlet of at least one stage filtration bottle through the filling pipeline (to realize multi-stage filling), and a switch and/or a filling driver for exporting water in the liquid storage vessel is arranged on the filling pipeline;

a separated material vessel being closed, the top or upper part of the separated material vessel is provided with an odor outlet and a material inlet communicating with the material outlet of the stage filter, and the bottom or lower part of the separated material vessel is provided with a bacterium liquid outlet;

a separate loading unit including at least one separate loading bottle, the top of the separate loading bottle is provided with a bacterium liquid inlet and a bacterium liquid outlet, the bacterium liquid inlet of the first separate loading bottle of the separate loading unit communicates with the bacterium liquid outlet of the separated material vessel through a bacterium liquid pipeline, and a bacterium liquid driver for importing bacterium liquid in the separated material vessel into the separate loading bottles is arranged on the bacterium liquid pipeline; and a deodorizer, provided with an odor inlet and an exhaust outlet, the odor inlet respectively communicates with the odor outlet of the raw material vessel and the odor outlet of the separated material vessel through an odor pipeline, and at least one buffer bottle for buffering and collecting liquid in odor and at least one gas pump for respectively importing odor in the raw material vessel and odor in the separated material vessel into the deodorizer are arranged on the odor pipeline.

The buffer bottle in the separator is of a vessel or bottle structure with a gas inlet and a gas outlet respectively arranged on the top or the upper part, and there can be one, two or more buffer bottles. In one solution, there are at least two buffer bottles on the odor pipeline, one of the buffer bottles is a liquid-sucking and deodorizing buffer bottle, and the gas inlet of the liquid-sucking and deodorizing buffer bottle is connected to the odor outlet of the raw material vessel; the other buffer bottle is a separating and deodorizing buffer bottle, and the gas inlet of the separating and deodorizing buffer bottle is connected to the odor outlet of the separated material vessel.

If there is one gas pump on the odor pipeline, an outlet of the gas pump is connected to the odor inlet of the deodorizer.

In one solution, if there are two or more gas pumps on the odor pipeline, a first gas pump for importing the odor in the raw material vessel into the deodorizer is arranged on the odor pipeline between the odor outlet of the raw material vessel and the gas inlet of the liquid-sucking and deodorizing buffer bottle or on the odor pipeline between the gas outlet of the liquid-sucking and deodorizing buffer bottle and the odor inlet of the deodorizer; and a second gas pump for importing the odor in the separated material vessel into the deodorizer and generating negative pressure in the separated material vessel is arranged on the odor pipeline between the odor outlet of the separated material vessel and the gas inlet of the separating and deodorizing buffer bottle or on the odor pipeline between the gas outlet of the separating and deodorizing buffer bottle and the odor inlet of the deodorizer.

In one solution, the water in the liquid storage vessel is imported respectively into the raw material vessel and the stage filtration bottles by switch-cooperating gravity flow or by driving power provided by the filling driver; the bacterium liquid driver and the filling driver are liquid peristaltic pumps; and the vibrator is a mechanical vibrator or an ultrasonic vibrator.

In one preferred solution, bacterium liquid inlet-connecting nipples are arranged at the bacterium liquid inlets of the separate loading bottles, bacterium liquid outlet-connecting nipples are arranged at the bacterium liquid outlets of the separate loading bottles, and the lower orifices of the bacterium liquid inlet-connecting nipples and the bacterium liquid outlet-connecting nipples respectively stretch into the separate loading bottles.

The top or upper part of the separated material vessel in the separator is provided with a bacterium liquid return inlet; if the separate loading unit includes one separate loading bottle, the bacterium liquid outlet of the separate loading bottle is connected to the bacterium liquid return inlet of the separated material vessel through a return pipeline; if the separate loading unit includes a plurality of separate loading bottles, all the separate loading bottles are connected in series, parallel or series and parallel, and the bacterium liquid outlet of the last separate loading bottle is connected to the bacterium liquid return inlet of the separated material vessel through the return pipeline.

If the stage filter in the separator includes a plurality of stage filtration bottles, each stage filtration bottle is connected to the discharge outlet of the previous stage filtration bottle and the feed inlet of the next stage filtration bottle in a series connection manner; and if the separate loading unit includes a plurality of separate loading bottles, each separate loading bottle is connected to the bacterium liquid outlet of the previous separate loading bottle and the bacterium liquid inlet of the next separate loading bottle in a series connection manner.

In one solution, the raw material vessel is provided with a feed inlet or a feed cover for cavitary contents; a filter screen is arranged under the agitator in the raw material vessel, and the discharge outlet of the raw material vessel is located under the filter screen.

In one solution, one or more layer (particularly two or more layers) of filter screens are arranged in each stage filtration bottle, and the filter screen is distributed in the form of a planar, convex, wavy, folding or U-shaped structure in the stage filtration bottle; and the filter hole diameters of the filter screens in the stage filter are reduced gradually within a range from 5.0 mm to 0.001 mm along a water flow direction.

In one solution, the liquid storage vessel is a water storage tank or bottle with at least one opening, or a tank which has the same internal structure as the raw material vessel and can substitute for the raw material vessel for use; the liquid outlet of the liquid storage vessel respectively communicates to the filling opening of the raw material vessel and the feed inlets of all or part of the stage filtration bottles through the filling pipeline, and the filling driver respectively adds water into the raw material vessel and the stage filtration bottles periodically or quantitatively.

In one solution, the deodorizer includes at least one deodorizing vessel which can remove odor in gas, and a material or substance which can for deodorize through a physical or chemical method is loaded in the deodorizing vessel; and if the deodorizer includes a plurality of deodorizing vessels, all the deodorizing vessels are connected in series, parallel or series and parallel.

Figure 2:
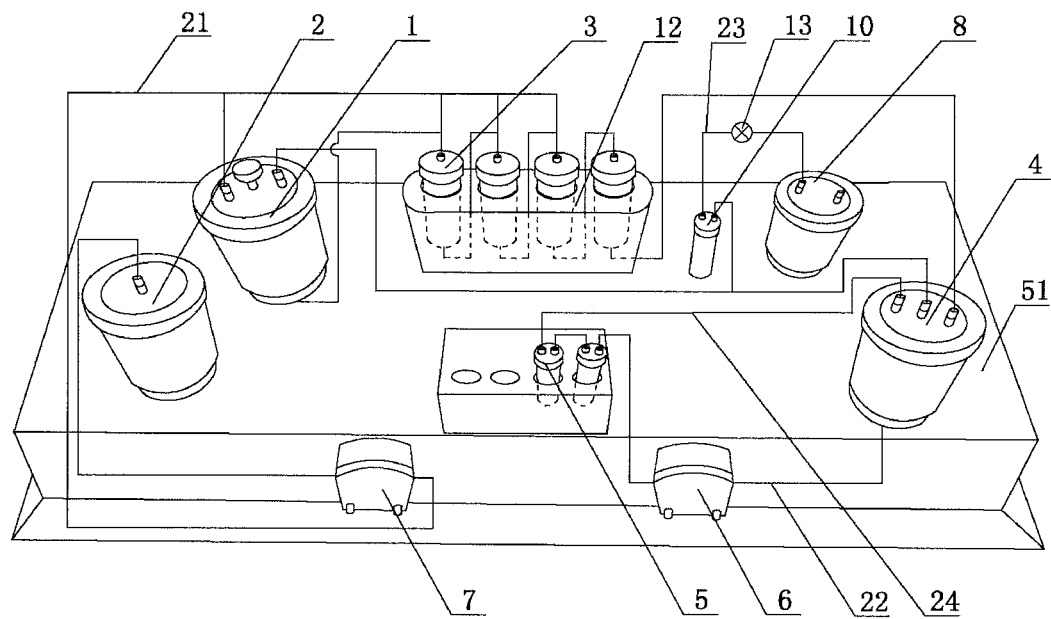

The beneficial effects of the present invention are as follows: by means of the organic combination of all the parts, the separator can realize the circular automatic filling of bacterium liquid, the bacterium liquid can be imported into the next separate loading bottle automatically after one separate loading bottle is filled up, consequently, manpower and operation steps are saved sufficiently, and the precision of operation is increased; by means of the stage filling of the liquid storage vessel, the separator realizes the dilution and suspension of fine particles, reduces bacterium content in impurities, and increases the bacterium collection rate and the purity of bacterium liquid, and it is discovered in an experiment that the quantity of extracted fore can be increased by stage filling in the stage filtration bottles by at least 5 to 10 percent. The whole apparatus and treatment space of the present invention do not produce odor, and the apparatus has high treatment efficiency, can save time and labor, is easy and convenient to operate, is more humanized, and has a good application prospect.

BRIEF DESCRIPTION OF THE DRAWINGS

FIG. 1 is a structural schematic diagram of a separator of the present invention.

FIG. 2 is another structural schematic diagram of the separator of the present invention.

FIG. 3 is a structural schematic diagram of a raw material vessel in the present invention.

FIG. 4 is a structural schematic diagram of a separate loading bottle in the present invention.

In the drawings, 1 is a raw material vessel, 2 is a liquid storage vessel, 3 is a stage filtration bottle, 4 is a separated material vessel, 5 is a separate loading bottle, 6 is a bacterium liquid driver, 7 is a filling driver, 8 is a deodorizer, 10 is a buffer bottle, 11 is a liquid-sucking and deodorizing buffer bottle, 12 is a vibrator, 13 is a gas pump, 14 is a separating and deodorizing buffer bottle, 21 is a filling pipeline, 22 is a bacterium liquid pipeline, 23 is an odor pipeline, 24 is a return pipeline, 31 is a second gas pump, 32 is a first gas pump, 41 is an agitator, 42 is a filter screen, 51 is an operating platform, 53 is a bacterium liquid outlet-connecting nipple, 54 is a bacterium liquid inlet-connecting nipple, 55 is a separate loading bottle cap, and 56 is a separate loading bottle body.

DETAILED DESCRIPTION

A separator of the present invention is further described in reference to the drawings and embodiments, but the scope of the present invention is limited to every following embodiment.

As shown in FIG. 1 or FIG. 2, the separator for microorganisms in cavitary contents in the present invention includes a raw material vessel 1, a stage filter, a liquid storage vessel 2, a separated material vessel 4, a separate loading unit, and a deodorizer 8. The upper part or top of the raw material vessel 1 is provided with a filling opening and an odor outlet, an agitator 41 is arranged in the raw material vessel 1, the lower part or bottom of the raw material vessel is provided with a discharge outlet, and the discharge outlet is connected to an inlet of a stage filter. The stage filter is provided with a material inlet and a material outlet, and the material inlet of the stage filter communicates with the discharge outlet of the raw material vessel. The stage filter mainly includes one or more stage filtration bottles 3, both ends of each stage filtration bottle are provided respectively with a feed inlet and a discharge outlet, and at least one layer of filter screen is arranged in each stage filtration bottle 3; if the stage filter includes multiple stage filtration bottles, all the stage filtration bottles are connected in series, parallel or series and parallel; the stage filter is arranged partially or completely in a vibrator 12 which can rock, shake or wave liquid in the stage filtration bottles. The liquid storage vessel 2 is provided with a liquid outlet, the liquid outlet of the liquid storage vessel communicates with the filling opening of the raw material vessel through a filling pipeline 21, or the liquid outlet communicates with both the filling opening of the raw material vessel and the feed inlet of at least one stage filtration bottle 3 through the filling pipeline 21, and a switch and/or a filling driver 7 for exporting water in the liquid storage vessel is arranged on the filling pipeline. The separated material vessel 4 is closed, the top or upper part of the separated material vessel is provided with an odor outlet and a material inlet communicating with the material outlet of the stage filter, and the bottom or lower part of the separated material vessel is provided with a bacterium liquid outlet. The separate loading unit includes at least one separate loading bottle 5, the top of the separate loading bottle 5 is provided with a bacterium liquid inlet and a bacterium liquid outlet, the bacterium liquid inlet of the first separate loading bottle of the separate loading unit communicates with the bacterium liquid outlet of the separated material vessel through a bacterium liquid pipeline, and a bacterium liquid driver for importing bacterium liquid in the separated material vessel into the separate loading bottles is arranged on the bacterium liquid pipeline. The deodorizer 8 is provided with an odor inlet and an exhaust outlet, the odor inlet of the deodorizer 8 respectively communicates with the odor outlet of the raw material vessel and the odor outlet of the separated material vessel through an odor pipeline 23, and at least one buffer bottle 10 for buffering and collecting liquid in odor and at least one gas pump 13 for respectively importing odor in the raw material vessel and odor in the separated material vessel into the deodorizer are arranged on the odor pipeline 12.

The buffer bottle 10 in the separator mainly prevents liquid or trace solid mixed in the odor from being imported directly into the deodorizer; and the buffer bottle can be utilized to buffer or collect part of the liquid or solid into the buffer bottle. If the defect does not exist, the whole collecting device can also include no buffer bottle. A common buffer bottle structure is a vessel or bottle structure with a gas inlet and a gas outlet respectively arranged on the top or the upper part. There can be one, two or more (more means more than two) buffer bottles. As shown in FIG. 2, in the solution adopting only one buffer bottle, the buffer bottle 10 can be arranged directly in front of the deodorizer 8, that is, the gas outlet of the buffer bottle 10 is connected to the odor inlet of the deodorizer 8 through a pipeline, or the gas outlet of the buffer bottle 10 is connected to the odor inlet of the deodorizer 8 through a pipeline and the gas pump 13. In order to achieve a better deodorizing effect, two or more buffer bottles can be arranged. As shown in FIG. 1, in one solution, there are at least two buffer bottles on the odor pipeline, one of the buffer bottles is a liquid-sucking and deodorizing buffer bottle 11, and the gas inlet of the liquid-sucking and deodorizing buffer bottle 11 is connected to the odor outlet of the raw material vessel through a pipeline or through a pipeline and a gas pump; the other buffer bottle is a separating and deodorizing buffer bottle 14, and the gas inlet of the separating and deodorizing buffer bottle 14 is connected to the odor outlet of the separated material vessel through a pipeline or through a pipeline and a gas pump. Other buffer bottles can be added on the deodorizing pipeline 23 as needed.

Besides importing the odor in the raw material vessel 1 and the separated material vessel 4 into the deodorizer 8, the gas pump on the odor pipeline 23 in the separator also generates negative pressure in the closed separated material vessel 4, and the negative pressure provides power to import liquid or suspension in the raw material vessel 1 into the separated material vessel 4 via the stage filter. It can also generate trace negative pressure in the unclosed raw material vessel 1, so that the odor can be completely imported into the deodorizer without directly spreading into the surrounding environment via the raw material vessel. As shown in FIG. 2, in one solution adopting only one gas pump, the outlet of the gas pump 13 is connected directly to the odor inlet of the deodorizer 8; and the gas pump in the separator can also be arranged at the gas outlet of the deodorizer.

In order to meet different conditions and achieve a best deodorizing effect, two or more gas pumps can be arranged. As shown in FIG. 1, in one solution, there are at least two gas pumps, the first gas pump 32 is arranged on the odor pipeline 23 between the odor outlet of the raw material vessel 1 and the gas inlet of the liquid-sucking and deodorizing buffer bottle 11 or arranged on the odor pipeline 23 between the gas outlet of the liquid-sucking and deodorizing buffer bottle 11 and the odor inlet of the deodorizer 8, and it imports the odor in the raw material vessel 1 into the deodorizer 8. The second gas pump 31 is arranged on the odor pipeline 23 between the odor outlet of the separated material vessel and the gas inlet of the separating and deodorizing buffer bottle 14 or arranged on the odor pipeline 23 between the gas outlet of the separating and deodorizing buffer bottle 14 and the odor inlet of the deodorizer, and the gas pump imports the odor in the separated material vessel into the deodorizer and generates negative pressure in the separated material vessel.

Figure 3:
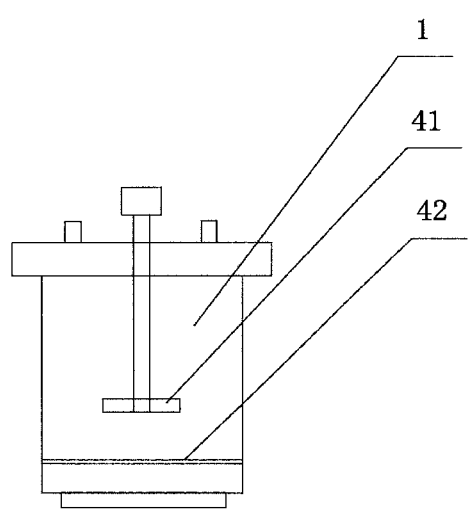

The raw material vessel of the separator is a unit for dispersing cavitary contents, soil, rivers, lakes or silt into liquid or suspension, and it can also have a preliminary filtering function by arranging a filter screen. The raw material vessel is provided with a feed inlet, a feed cover or other feeders for materials such as cavitary contents; the agitator is arranged in the raw material vessel, and the agitator can be a mechanical agitator or a magnetic agitator. As shown in FIG. 3, in one solution, a filter screen 42 is arranged under the agitator 41 in the raw material vessel, while the discharge outlet of the raw material vessel is located under the filter screen 42. The bottom of the raw material vessel 1 can be of a planar structure, or can be of a downwards concave slope structure, a cambered surface structure or a stepped structure, the appearance of the raw material vessel can be a round barrel, a flat barrel, a cube, a cuboid or of an irregular shape, and the raw material vessel is not closed. The raw material vessel in a working state is vertical.

As shown in FIG. 2, the liquid storage vessel 2 in the separator can be a water storage tank or bottle with at least one opening, and it's only used to supply water, normal saline or other needed liquids; as shown in FIG. 1, the liquid storage tank can also be a tank which has the same internal structure as the raw material vessel and can substitute for the raw material vessel for use, and thus it is used to supply water or other liquids under the normal state, and can directly substitute for the raw material vessel for use when the raw material vessel operates unstably or is damaged.

The liquid outlet of the liquid storage vessel 2 communicates to the filling opening of the raw material vessel 1 through the filling pipeline, or the liquid outlet of the liquid storage vessel 2 respectively communicates to the filling opening of the raw material vessel 1 and the feed inlets of all or part of the stage filtration bottles 3. As shown in FIG. 1 and FIG. 2, in one preferred solution, the liquid outlet of the liquid storage vessel communicates to both the filling opening of the raw material vessel and the feed inlets of part of the stage filtration bottles to implement stage filling. The water or liquid in the liquid storage vessel 2 can be added periodically or quantitatively into the raw material vessel 1 or the stage filtration bottles 3 by switch-cooperating gravity flow, or the filling driver 7 can respectively add liquid (such as normal saline) into the raw material vessel 1 and the stage filtration bottles 3 periodically or quantitatively. According to specific circumstances, liquid can be added selectively into all or part of the stage filtration bottles to dilute materials in the stage filtration bottles, consequently, more target florae can more easily pass through each stage of filter screen, the bacterium content in unfiltered impurities is reduced, and the flora collection rate is increased. A variety of conventional liquid drivers, such as a liquid peristaltic pump, can be adopted as the filling driver 7 in the separator.

The stage filter in the separator can include one stage filtration bottle 3, or can include multiple (two or more) stage filtration bottles 3. Both ends of each stage filtration bottle are provided respectively with a feed inlet and a discharge outlet, and when the stage filtration bottle is arranged vertically or obliquely, the feed inlet and the discharge outlet are located respectively at the upper end (i.e. the top or the upper part) and the lower end (i.e. the bottom or the lower part) of the stage filtration bottle or the lower end and the upper end of the stage filtration bottle; and when the stage filtration bottle is arranged horizontally, the feed inlet and the discharge outlet are located respectively at the left end or right end of the stage filtration bottle. As shown in FIG. 1 and FIG. 2, in one preferred solution, the stage filter includes multiple stage filtration bottles, and at this point, all the stage filtration bottles can be connected in series, parallel or series and parallel; and in the solution of FIG. 1 and FIG. 2, each stage filtration bottle is connected to the discharge outlet of the previous stage filtration bottle and the feed inlet of the next stage filtration bottle in a series connection manner.

More than one layer of filter screen is arranged in each stage filtration bottle 3, and in one preferred solution, two or more layers of filter screens can be arranged. The filter screens in each stage filtration bottle 3 can be distributed in the form of a planar, convex, wavy, folding or U-shaped structure in the bottle; each filter screen can be shaped like an inverted trapeziform strip-shaped trough with an upward opening, and the surface of the inverted trapeziform strip-shaped trough is of a filter screen structure; one side of the upper side of the suspension container is provided with openings for the horizontal insertion of the inverted trapeziform strip-shaped troughs, and a closed structure is formed by positioning in a fastening or screwing manner. Such a form of filter screen can be conveniently inserted and taken out like a "drawer" structure, and can also be provided with a handle. The bottom (or one end) of each stage filtration bottle can be a plane, or can be an outwardly raised cambered surface.

The filter hole diameters of the filter screens in the stage filter are reduced gradually within a range from 5.0 mm to 0.001 mm along a water flow direction. According to the requirement of actual clinical filtration, preferably all the stages of filter parts have the same size and shape, only the hole diameters of the filter screens are different, and thereby filter screens with different hole diameters can be replaced conveniently, or false filter parts (no filter screens or large-diameter filter screens without filtering purpose) can be utilized for replacement to reduce filtering layers. The design can enable the filter screens with specific filter hole diameter to collect target components. Therefore, when the number of the stage filtration bottles in the stage filter is reduced, the number of the filter screens in a single stage filtration bottle can be increased accordingly.

When the stage filter includes only one stage filtration bottle, the feed inlet of the stage filtration bottle is the material inlet of the stage filter, and the discharge outlet of the stage filtration bottle is the material outlet of the stage filter. When the stage filter includes multiple stage filtration bottles, the feed inlet of the first stage filtration bottle (connected in series) or the first group of stage filtration bottles (connected in parallel) is the material inlet of the stage filter, and the discharge outlet of the last stage filtration bottle (connected in series) or the last group of stage filtration bottles (connected in parallel) is the material outlet of the stage filter; of course, when the multiple stage filtration bottles are connected in a more complex manner, the material inlet and the material outlet of the stage filter can be distinguished according to the general viewpoint of those skilled in the art.

All or part of the stage filtration bottles 3 in the stage filter can be arranged on a vibrator 12, so that the liquid in the stage filtration bottles 3 can be vibrated sufficiently during filtration in order to promote the effect of filtration; and the vibrator 12 can be a mechanical vibrator, an ultrasonic vibrator or the like.

The separated material vessel 4 in the separator is a closed container which is used to temporarily store bacterium liquid obtained by layer-by-layer filtration. The top or upper part of the separated material vessel 4 is provided with an odor outlet, a material inlet and a bacterium liquid return inlet; and a negative pressure state is generated in the separated material vessel 4 by the gas pump, so that the liquid is filtered layer by layer and converges into the separated material vessel.

The separate loading unit in the separator includes at least one separate loading bottle 5. If the separate loading unit includes one separate loading bottle, the bacterium liquid outlet of the separate loading bottle is connected to the bacterium liquid return inlet of the separated material vessel through a return pipeline; if the separate loading unit includes multiple separate loading bottles, all the separate loading bottles are connected in series, parallel or series and parallel, and the bacterium liquid outlet of the last separate loading bottle is connected to the bacterium liquid return inlet of the separated material vessel through the return pipeline. Such a connection method can enable bacterium liquid to fill up one or more separated material vessels and make the redundant bacterium liquid return into the separated material vessel via the return pipeline. The bacterium liquid driver for importing the bacterium liquid in the separated material vessel into the separate loading bottles is arranged on the bacterium liquid pipeline, and a variety of conventional liquid drivers, such as a liquid peristaltic pump, can be adopted as the bacterium liquid driver. Connection methods for the multiple separate loading bottles in the separate loading unit can be determined according to specific circumstances, and in the solution of FIG. 1 and FIG. 2, each separate loading bottle is connected to the bacterium liquid outlet of the previous separate loading bottle and the bacterium liquid inlet of the next separate loading bottle in a series connection manner.

Figure 4:
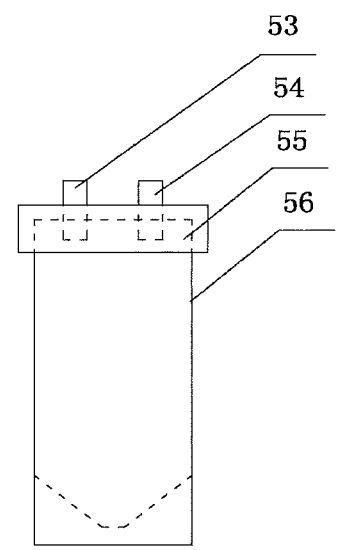

The top of each separate loading bottle 5 is provided with a bacterium liquid inlet and a bacterium liquid outlet, as shown in FIG. 4, in one preferred solution, the separate loading bottle includes a separate loading bottle body 56 and a separate loading bottle cap 55, the cap is provided with a bacterium liquid inlet and a bacterium liquid outlet, wherein a bacterium liquid inlet-connecting nipple 54 is arranged at the bacterium liquid inlet of the cap, a bacterium liquid outlet-connecting nipple 53 is arranged at the bacterium liquid outlet of the separate loading bottle, and the lower orifices of the bacterium liquid inlet-connecting nipple 54 and the bacterium liquid outlet-connecting nipple 53 respectively stretch into the separate loading bottle body. Such a structure can prevent the bacterium liquid in the separate loading bottle from being too full to affect the subsequent treatment of the bacterium liquid.

The deodorizer 8 in the separator includes at least one deodorizing vessel which can remove odor in gas, and a variety of conventional materials or substances which can deodorize through a physical or chemical method is loaded in the deodorizing vessel; and if the deodorizer includes multiple deodorizing vessels, all the deodorizing vessels are connected in series, parallel or series and parallel. The separator utilizes the buffer bottles, the gas pumps and the odor pipeline to collect odor produced in the whole separator, and treats the odor in time to prevent odor production.

Taking FIG. 1 as an example, when the separator operates, cavitary contents are first put into the raw material vessel 1, the filling driver 7 quantitatively adds water in the liquid storage vessel 2 into the raw material vessel 1 via the filling pipeline, and the agitator 41 in the raw material vessel 1 mixes the cavitary contents into liquid or suspension. At the same time, the first gas pump 32 is switched on to suck odor, the second gas pump 31 is also switched on, so that negative pressure is generated in the separated material vessel 4 (by first utilizing some switching parts to close some passages of the separated material vessel 4), the liquid or suspension in the raw material vessel 1 is imported into the stage filtration bottles 3 under the drive of the negative pressure after being filtered preliminarily, and filtered layer by layer by the gradually reduced filter screen hole diameter in each stage filtration bottle 3 connected in series, and bacterium liquid with bacterium diameter matching predetermined filter holes is separated out of the last stage filtration bottle 3. In the process of stage filtration, the vibrator 12 sufficiently vibrates or shakes the liquid that is being filtered, so that the effect of filtration can be enhanced, and at the same time, the filling driver 7 adds liquid into the different stage filtration bottles 3 via the filling pipeline 21 to dilute the liquid, so that the effect of filtration can be further enhanced. The bacterium liquid which is filtered out stage by stage is sucked into the separated material vessel 4 and collected. When a certain amount of bacterium liquid has been collected, under the condition of starting or stopping multi-stage filtration, the bacterium liquid driver 6 is switched on to import the bacterium liquid into the separate loading bottles 5 via the bacterium liquid pipeline 22 to fill up every separate loading bottle 5 in sequence, and the redundant bacterium liquid returns into the separated material vessel 4 via the return pipeline 24. After filling is complete, every separate loading bottle is taken out for subsequent treatment. In the process of multi-stage filtration and filling, under the action of the first gas pump 32, the odor produced by the raw material vessel 1 and liquid probably splashing out during agitation are sucked into the liquid-sucking and deodorizing buffer bottle 11, and after trace liquid and solid are removed in the liquid-sucking and deodorizing buffer bottle 11, the odor is imported into the deodorizer for deodorization; and at the same time, under the action of the second gas pump 31, the odor in the separated material vessel 4 or liquid that splashes out is sucked into the separating and deodorizing buffer bottle 14, so that the odor from which the liquid is removed is further imported into the deodorizer for deodorization.

If the deodorizer 8, the buffer bottles, the separate loading unit, the liquid storage vessel 2 and the filling pipeline 21 and the bacterium liquid driver 6 for stage filling in FIG. 1 are removed, a simple collecting apparatus for comparison is obtained. Although the simple collecting apparatus still has the effect of separating out a certain amount of cavitary contents, under the condition of the same cavitary content amount, the extracted bacterium amount of the apparatus is 10 percent lower than that of the separator in FIG. 1, and twenty to thirty black particle impurities can be seen in collected bacterium liquid under a single field of view in a gastroscope, while, for the separator, there is only zero to one black particle impurity under the single field of view in the gastroscope The simple collecting apparatus can leak out a lot of odor in the process of collection, a lot of time is taken to separately load bacterium liquid, and the operation process can hardly meet the requirement of humanization. On the contrary, the separator won't leak out odor, separation and filling are timesaving, simple and convenient, fifteen minutes can be saved on average in tall in each separation process, the mortality of florae in the aerobic environment in vitro is reduced, and thereby the therapeutic effect is increased.

What is claimed is:

1. A separator for microorganisms in cavitary contents, comprising:
   a raw material vessel, provided with a filling opening and an odor outlet, an agitator is arranged in the raw material vessel, a lower part or bottom of the raw material vessel is provided with a discharge outlet, and the discharge outlet is connected to an inlet of a stage filter;
   a stage filter, provided with a material inlet and a material outlet, the material inlet of the stage filter communicates with the discharge outlet of the raw material vessel, the stage filter mainly comprises one or more stage filtration bottles, both ends of each stage filtration bottle are provided respectively with a feed inlet and a discharge outlet, and at least one layer of filter screen is arranged in each stage filtration bottle; if the stage filter comprises a plurality of stage filtration bottles, all the stage filtration bottles are connected in series, parallel or series and parallel; the stage filter is arranged partially or completely in a vibrator which can rock, shake or wave liquid in the stage filtration bottles;
   a liquid storage vessel, provided with a liquid outlet, the liquid outlet communicates with the filling opening of the raw material vessel through a filling pipeline, or the liquid outlet communicates with both the filling opening of the raw material vessel and the feed inlet of at least one stage filtration bottle through the filling pipeline, and a switch and/or a filling driver for exporting water in the liquid storage vessel is arranged on the filling pipeline;
   a separated material vessel, being closed, a top or upper part of the separated material vessel is provided with an odor outlet and a material inlet communicating with the material outlet of the stage filter, and the bottom or lower part of the separated material vessel is provided with a bacterium liquid outlet;
   a separate loading unit, comprising at least one separate loading bottle, a top of the separate loading bottle is provided with a bacterium liquid inlet and a bacterium liquid outlet, the bacterium liquid inlet of the first separate loading bottle of the separate loading unit communicates with the bacterium liquid outlet of the separated material vessel through a bacterium liquid pipeline, and a bacterium liquid driver for importing bacterium liquid in the separated material vessel into the separate loading bottles is arranged on the bacterium liquid pipeline;
   and a deodorizer, provided with an odor inlet and an exhaust outlet, the odor inlet respectively communicates with the odor outlet of the raw material vessel and the odor outlet of the separated material vessel through an odor pipeline, and at least one buffer bottle for buffering and collecting liquid in odor and at least one gas pump for respectively importing odor in the raw material vessel and odor in the separated material vessel into the deodorizer are arranged on the odor pipeline.

2. The separator for microorganisms in cavitary contents according to claim 1, wherein the buffer bottle is of a vessel or bottle structure with a gas inlet and a gas outlet respectively arranged on the top or the upper part, and there can be one, two or more buffer bottles.

3. The separator for microorganisms in cavitary contents according to claim 2, wherein there are at least two buffer bottles on the odor pipeline, one of the buffer bottles is a liquid-sucking and deodorizing buffer bottle, and the gas inlet of the liquid-sucking and deodorizing buffer bottle is connected to the odor outlet of the raw material vessel; the other buffer bottle is a separating and deodorizing buffer bottle, and the gas inlet of the separating and deodorizing buffer bottle is connected to the odor outlet of the separated material vessel.

4. The separator for microorganisms in cavitary contents according to claim 3, wherein there are two or more gas pumps on the odor pipeline, a first gas pump for importing the odor in the raw material vessel into the deodorizer is arranged on the odor pipeline between the odor outlet of the raw material vessel and the gas inlet of the liquid-sucking and deodorizing buffer bottle or on the odor pipeline between the gas outlet of the liquid-sucking and deodorizing buffer bottle and the odor inlet of the deodorizer; and a second gas pump for importing the odor in the separated material vessel into the deodorizer and generating negative pressure in the separated material vessel is arranged on the odor pipeline between the odor outlet of the separated material vessel and the gas inlet of the separating and deodorizing buffer bottle or on the odor pipeline between the gas outlet of the separating and deodorizing buffer bottle and the odor inlet of the deodorizer.

5. The separator for microorganisms in cavitary contents according to claim 2, wherein there is one gas pump on the odor pipeline, an outlet of the gas pump is connected to the odor inlet of the deodorizer.

6. The separator for microorganisms in cavitary contents according to claim 1, wherein the water in the liquid storage vessel is imported respectively into the raw material vessel and the stage filtration bottles by switch-cooperating gravity flow; the bacterium liquid driver and the filling driver are liquid peristaltic pumps; and the vibrator is a mechanical vibrator or an ultrasonic vibrator.

7. The separator for microorganisms in cavitary contents according to claim 1, wherein bacterium liquid inlet-connecting nipples are arranged at the bacterium liquid inlets of the separate loading bottles, bacterium liquid outlet-connecting nipples are arranged at the bacterium liquid outlets of the separate loading bottles, and the lower orifices of the bacterium liquid inlet-connecting nipples and the bacterium liquid outlet-connecting nipples respectively stretch into the separate loading bottles.

8. The separator for microorganisms in cavitary contents according to claim 1, wherein the top or upper part of the separated material vessel is provided with a bacterium liquid return inlet; the separate loading unit comprises one separate loading bottle, the bacterium liquid outlet of the separate loading bottle is connected to the bacterium liquid return inlet of the separated material vessel through a return pipeline.

9. The separator for microorganisms in cavitary contents according to claim 1, wherein the stage filter comprises a plurality of stage filtration bottles, each stage filtration bottle is connected to the discharge outlet of the previous stage filtration bottle and the feed inlet of the next stage filtration bottle in a series connection manner; and the separate loading unit comprises a plurality of separate loading bottles, each separate loading bottle is connected to the bacterium liquid outlet of the previous separate loading bottle and the bacterium liquid inlet of the next separate loading bottle in a series connection manner.

10. The separator for microorganisms in cavitary contents according to claim 1, wherein the raw material vessel is provided with a feed inlet or a feed cover for cavitary contents; a filter screen is arranged under the agitator in the raw material vessel, and the discharge outlet of the raw material vessel is located under the filter screen.

11. The separator for microorganisms in cavitary contents according to claim 1, wherein two or more layers of filter screens are arranged in each stage filtration bottle, and the filter screens are distributed in the form of a planar, convex, wavy, folding or U-shaped structure in the stage filtration bottle; and the filter hole diameters of the filter screens in the stage filter are reduced gradually within a range from 5.0 mm to 0.001 mm along a water flow direction.

12. The separator for microorganisms in cavitary contents according to claim 1, wherein the liquid storage vessel is a water storage tank or bottle with at least one opening, or a tank which has the same internal structure as the raw material vessel and can substitute for the raw material vessel for use; the liquid outlet of the liquid storage vessel respectively communicates to the filling opening of the raw material vessel and the feed inlets of all or part of the stage filtration bottles through the filling pipeline, and the filling driver respectively adds water into the raw material vessel and the stage filtration bottles periodically or quantitatively.

13. The separator for microorganisms in cavitary contents according to claim 1, wherein the deodorizer comprises at least one deodorizing vessel which can remove odor in gas, and a material or substance which can deodorize through a physical or chemical method is loaded in the deodorizing vessel.

14. The separator for microorganisms in cavitary contents according to claim 13, wherein the deodorizer comprises a plurality of deodorizing vessels, all the deodorizing vessels are connected in series, parallel or series and parallel.

15. The separator for microorganisms in cavitary contents according to claim 1, wherein the stage filter comprises a plurality of stage filtration bottles, each stage filtration bottle is connected to the discharge outlet of the previous stage filtration bottle and the feed inlet of the next stage filtration bottle in a series connection manner; and the separate loading unit comprises a plurality of separate loading bottles, each separate loading bottle is connected to the bacterium liquid outlet of the previous separate loading bottle and the bacterium liquid inlet of the next separate loading bottle in a series connection manner.

16. The separator for microorganisms in cavitary contents according to claim 1, wherein the water in the liquid storage vessel is imported respectively into the raw material vessel and the stage filtration bottles by driving power provided by the filling driver; the bacterium liquid driver and the filling driver are liquid peristaltic pumps; and the vibrator is a mechanical vibrator or an ultrasonic vibrator.

17. The separator for microorganisms in cavitary contents according to claim 1, wherein the top or upper part of the separated material vessel is provided with a bacterium liquid return inlet; the separate loading unit comprises a plurality of separate loading bottles, all the separate loading bottles are connected in series, parallel or series and parallel, and the bacterium liquid outlet of the last separate loading bottle is connected to the bacterium liquid return inlet of the separated material vessel through a return pipeline.

* * * * *